US011332514B2

(12) United States Patent
Falkenstein et al.

(10) Patent No.: US 11,332,514 B2
(45) Date of Patent: May 17, 2022

(54) CATION AND ANION EXCHANGE CHROMATOGRAPHY METHOD

(71) Applicant: Hoffmann-La Roche Inc., Little Falls, NJ (US)

(72) Inventors: Roberto Falkenstein, Munich (DE); Maria Laura Magri, Penzberg (DE); Michaela Mehr, Uffing (DE); Klaus Schwendner, Weilheim (DE); Bernhard Spensberger, Eberfing (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 571 days.

(21) Appl. No.: 14/920,127

(22) Filed: Oct. 22, 2015

(65) Prior Publication Data

US 2016/0237140 A1  Aug. 18, 2016

Related U.S. Application Data

(63) Continuation of application No. 13/588,281, filed on Aug. 17, 2012, now abandoned.

(30) Foreign Application Priority Data

Aug. 25, 2011 (EP) .................................... 11178745
Oct. 4, 2011 (EP) .................................... 11183862

(51) Int. Cl.
   *C07K 14/775* (2006.01)
   *C07K 1/18* (2006.01)
   *B01D 15/36* (2006.01)

(52) U.S. Cl.
   CPC .......... *C07K 14/775* (2013.01); *B01D 15/362* (2013.01); *B01D 15/363* (2013.01); *C07K 1/18* (2013.01)

(58) Field of Classification Search
   CPC ...... C07K 14/775; C07K 1/18; B01D 15/362; B01D 15/363
   See application file for complete search history.

(56) References Cited

U.S. PATENT DOCUMENTS

| | | | |
|---|---|---|---|
| 4,129,560 A | 12/1978 | Zoltobrocki | |
| 5,463,029 A | 10/1995 | Dunn et al. | |
| 6,451,987 B1 | 9/2002 | Staby | |
| 2002/0156007 A1 | 10/2002 | Graversen et al. | |
| 2003/0229212 A1 | 12/2003 | Fahrner et al. | |
| 2006/0234226 A1 | 10/2006 | Fahner et al. | |
| 2009/0286960 A1* | 11/2009 | Hoang ................. | C07K 14/775 530/359 |
| 2010/0190210 A1* | 7/2010 | Arunakumari ........... | C07K 1/18 435/69.6 |
| 2010/0285530 A1 | 11/2010 | Humphreys et al. | |
| 2011/0263834 A1* | 10/2011 | Lees ........................ | C07K 1/16 530/399 |

FOREIGN PATENT DOCUMENTS

| | | |
|---|---|---|
| EP | 0013826 A1 | 8/1980 |
| EP | 0530477 A1 | 3/1993 |
| EP | 10008993.7 | 8/2010 |
| EP | 10188392.4 | 10/2010 |
| EP | 12157510.4 | 2/2012 |
| EP | 12157512.0 | 2/2012 |
| EP | 12157513.8 | 2/2012 |
| EP | 12162810.1 | 4/2012 |
| EP | 12162814.3 | 4/2012 |
| WO | 89/05157 | 6/1989 |
| WO | 2004/024866 A2 | 3/2004 |
| WO | 2004/026251 A2 | 4/2004 |
| WO | 2004/031213 A1 | 4/2004 |
| WO | 2008/002235 A1 | 1/2008 |
| WO | 2008/088403 A2 A2 | 7/2008 |
| WO | 2010/063717 A1 | 6/2010 |
| WO | 2012/007495 A1 | 1/2012 |
| WO | 2012/028522 A1 | 3/2012 |
| WO | 2012/028523 A2 | 3/2012 |
| WO | 2012/028525 A2 | 3/2012 |
| WO | 2012/028526 A2 | 3/2012 |

(Continued)

OTHER PUBLICATIONS

Kolk & Samuel, Isolation, Chemical and Immunological Characterization of Two Strongly Basic Nuclear Proteins from Human Spermatozoa, Biochimica et Biophysica Acta, 393 (1975) 307-319.*
Cole, Jl. of Biol. Chem., vol. 235 No. 8, Aug. 1960, pp. 2294-2299.*
Hplc of Biological Macro-Molecules, Revised and Expanded, edited by Karen M. Gooding, Fred E. Regnier, CRC Press, Jan. 2002, excerpt of p. 429 provided as PDF, one page provided.*
Kolk & Samuel, Isolation, Chemical and Immunological Characterization of Two Strongly Basic Nuclear Proteins from Human Spermatozoa, Biochimica et Biophysica Acta, 393 (1975) 307-319 (Year: 1975).*

(Continued)

*Primary Examiner* — Fred H Reynolds
*Assistant Examiner* — Joseph Fischer
(74) *Attorney, Agent, or Firm* — Morrison & Foerster LLP

(57) ABSTRACT

Herein is reported a method for purifying a polypeptide comprising the steps of i) applying a solution comprising the polypeptide to an ion exchange chromatography material, and ii) recovering the polypeptide with a solution comprising a denaturant and thereby purifying the polypeptide, whereby the ion exchange chromatography material comprises a matrix of cross-linked poly (styrene-divinylbenzene) to which ionic ligands have been attached, and wherein the solution comprising the polypeptide applied to the ion exchange chromatography material is free of the denaturant and the polypeptide adsorbed to the ion exchange chromatography material is recovered with a solution comprising a denaturant at a constant conductivity.

22 Claims, 8 Drawing Sheets

Specification includes a Sequence Listing.

(56) References Cited

FOREIGN PATENT DOCUMENTS

WO    WO-2012028526 A2 *    3/2012    ............... A61P 9/00
WO    PCT/EP2012/066301        8/2012

OTHER PUBLICATIONS

Sep. 8, 2015 EPO office communication for Application No. 12 7 4 8 6 8 9. 2, , 2 pages (Year: 2015).*
Hplc of Biological Macro-Molecules, Revised and Expanded, edited by Karen M. Gooding, Fred E. Regnier, CRC Press, Jan. 2002, excerpt of p. 429 provided as PDF, one page (previously) provided. (Year: 2002).*
Demain and Vaishnav, Biotechnology Advances 27 (2009) 297-306 (Year: 2009).*
Gudiksen et al., PNAS May 23, 2006 vol. 103 No. 21, 7968-7972 (Year: 2006).*
Mohan, Calbiochem Buffers, 2003, 37 pages (Year: 2003).*
Paul Wingfield, Current Protocols in Protein Science (2002) 6.1.1-6.1.37 (Year: 2002).*
GE Healthcare Ion Exchange Chromatograph and Chromatofocusing, 187 p. 2010 (Year: 2010).*
Li et al., Journal of Chromatography A, 959 (2002) 113-120 (Year: 2002).*
Cole, J. Biol. Chem., vol. 235, No. 8, Aug. 1960, 2294-2299 (Year: 1960).*
Tran et al., Chromatographia 2007, 66, November (No. 9/10), 709-715 (Year: 2007).*
Yan et al., (1998) J Chromatogr A 813:187-200 12 (Year: 1998).*
Nadler et al., (1996) J Chromatogr A 743:91-98 13 (Year: 1996).*
Hplc of Biological Macro-Molecules, Revised and Expanded, edited by Karen M. Gooding, Fred E. Regnier, CRC Press, Jan. 2002, excerpt from p. 429 (Year: 2002).*
Agilent Anion-Exchange Media for Proteins, 2011, 9 pages (Year: 2011).*
Hunter et al., Journal of Chromatography A, 1204 (2008) 42-47 (Year: 2008).*
Miller, W.L., and J.D. Baxter: Synthesis of biologically active proteins by recombinant DNA technology. Drug Dev. Res. 1:435-454, 1981 (Year: 1981).*
Q Sepharose Data File 18-1172-88 AB, 8 pages 2006 (Year: 2006).*
Angarita et al., Journal of Chromatography A, vol. 1354, Aug. 8, 2014, pp. 18-25 (Year: 2014).*
Kolk and Samuel, Bichimica et Biphysica Acta, 393 (1975) 307-319 (Year: 1975).*
Kumaran and Ramamurthy, J Fluoresc (2011) 21:1499-1508 (Year: 2011).*
Bird et al., "Single-Chain Antigen-Binding Proteins" Science 242:423-426 (Oct. 21, 1988).
Chromedia, screenshot of http://www.chromedia.org/chromedia?waxtrapp=zjmmmEsHonOvmOllEwCcDmK (2015).
Cole, "The Chromatography of Insulin in Urea-Containing Buffer" Journal of Biological Chemistry 235(8):2294-2299 (1960).
Danielsson et al., "One-Step Purification of Monoclonal IgG Antibodies from Mouse Ascites" Journal of Immunological Methods 115:79-88 (1988).
Encyclopedia of Chemical Technology, "Ion Exchange" Kroschwitz, ed., fourth edition, New York: John Wiley & Sons, vol. 14:737-783 (1993).
Gu et al., "Urea Gradient Size-Exclusion Chromatography Enhanced the Yield of Lysozyme Refolding" Journal of Chromatography A 918:311-318 (2001).
Hood et al., Immunology 2nd edition, The Benjamin/Cummings Publishing Company, Inc., Menlo Park, California:2 pages (1984).
Hunkapiller et al., "The Growing Immunoglobulin Gene Superfamily" Nature 323:15-16. (Sep. 4, 1986).
Huston et al., "Protein Engineering of Antibody Binding Sites: Recovery of Specific Activity in an Anti-Digoxin Single-Chain Fv Analogue Produced in *Escherichia coli*" Proc. Natl. Acad. Sci. USA 85:5879-5883 (Aug. 1988).
Khademi et al., "Effect of Urea on Protein Separation by Ion-Exchange Chromatography" Journal of Biochemistry 147(5):735-741 (2010).
Kolk et al., "Isolation, Chemical and Immunological Characterization of Two Strongly Basic Nuclear Proteins from Human Spermatozoa" Biochimica et Biophysica Acta 393:307-319 (1975).
Lim et al., "Urea, but not Guanidinium, Destabilizes Proteins by Forming Hydrogen Bonds to the Peptide Group" PNAS 106(8):2595-2600 (Feb. 24, 2009).
Lin et al., "Refolding of Reduced/Denatured Bovine Pancreatic Insulin with Ion-Exchange Chromatography Coupled with MALDI-TOF MS" Chinese Chemical Letters 20:1487-1490 (2009).
Merrick et al., "A Complete System for Quantitative Analysis of Total DNA, Protein Impurities and Relevant Proteins" Biotech Forum Europe 9(6):398-403 (Jun. 1992).
MSDS of Bio-Rex Resin, 70 Sodium, OSHA HCS, 6 pages (Printing Date Jan. 7, 2015).
MSDS of Guanidine Hydrochloride (G8371), Mallinckrodt Baker, Inc., 4 pages (Effective Date Dec. 8, 1996).
Necina et al., "Capture of Human Monoclonal Antibodies from Cell Culture Supernatant by Ion Exchange Media Exhibiting High Charge Density" Biotechnology and Bioengineering 60(6):689-698 (Dec. 20, 1998).
Norburg et al., "A Cation-Exchange Material for Protein Separations Based on Grafting of Thiol-Terminated Sulfopropyl Methacrylate Telomers onto Hydrophilized Monodisperse Divinylbenzene Particles" (Abstract) Journal of Separation Science, 31(12) (Jul. 2008).
Protein Function, a Practical Approach "Folding Proteins" Rudolph, et al., Oxford:IRL Press:57-99 (1997).
Protein Sequence of *Homo sapiens* Proapolipoprotein, Reference gb/AAA51747.1.
Singh et al., "Solubilization and Refolding of Bacterial Inclusion Body Proteins" Journal of Bioscience and Bioengineering 99(4):303-310 (2005).
Vijayalakshmi, "Antibody Purification Methods" Applied Biochemistry and Biotechnology 75:93-102 (1998).
Wang et al., "High-Level Expression of Human TFF3 in *Escherichia coli*" Peptides 26:1213-1218 (2005).
Wang et al., "On-Column Refolding of Consensus Interferon at High Concentration with Guanidine-Hydrochloride and Polyethylene Glycol Gradients" Journal of Chromatography A 1115:72-80 (2006).
Wang et al., "Urea-Gradient Protein Refolding in Size Exclusion Chromatography" Current Pharmaceutical Biotechnology 11:289-292 (2010).
Graversen, "Trimerization of Apolipoprotein A-I Retards Plasma Clearance and Preserves Antiatheroselerotic Properties" Cardiovasc Pharmacol 51(2):170-177 (Feb. 2008).

* cited by examiner

SEQUENCE LISTING

<160> NUMBER OF SEQ ID NOS: 4

<210> SEQ ID NO 1
<211> LENGTH: 284
<212> TYPE: PRT
<213> ORGANISM: Artificial Sequence
<220> FEATURE:
<223> OTHER INFORMATION: Tetranectin-apolipoprotein A-I (1)

<400> SEQUENCE: 1

```
Pro Ile Val Asn Ala Lys Lys Asp Val Val Asn Thr Lys Met Phe Glu
1               5                   10                  15

Glu Leu Lys Ser Arg Leu Asp Thr Leu Ala Gln Glu Val Ala Leu Leu
            20                  25                  30

Lys Glu Gln Gln Ala Leu Gln Thr Val Asp Glu Pro Pro Gln Ser Pro
        35                  40                  45

Trp Asp Arg Val Lys Asp Leu Ala Thr Val Tyr Val Asp Val Leu Lys
    50                  55                  60

Asp Ser Gly Arg Asp Tyr Val Ser Gln Phe Glu Gly Ser Ala Leu Gly
65                  70                  75                  80

Lys Gln Leu Asn Leu Lys Leu Leu Asp Asn Trp Asp Ser Val Thr Ser
                85                  90                  95

Thr Phe Ser Lys Leu Arg Glu Gln Leu Gly Pro Val Thr Gln Glu Phe
            100                 105                 110

Trp Asp Asn Leu Glu Lys Glu Thr Glu Gly Leu Arg Gln Glu Met Ser
        115                 120                 125

Lys Asp Leu Glu Glu Val Lys Ala Lys Val Gln Pro Tyr Leu Asp Asp
    130                 135                 140

Phe Gln Lys Lys Trp Gln Glu Glu Met Glu Leu Tyr Arg Gln Lys Val
145                 150                 155                 160

Glu Pro Leu Arg Ala Glu Leu Gln Glu Gly Ala Arg Gln Lys Leu His
                165                 170                 175

Glu Leu Gln Glu Lys Leu Ser Pro Leu Gly Glu Glu Met Arg Asp Arg
            180                 185                 190

Ala Arg Ala His Val Asp Ala Leu Arg Thr His Leu Ala Pro Tyr Ser
        195                 200                 205

Asp Glu Leu Arg Gln Arg Leu Ala Ala Arg Leu Glu Ala Leu Lys Glu
    210                 215                 220

Asn Gly Gly Ala Arg Leu Ala Glu Tyr His Ala Lys Ala Thr Glu His
225                 230                 235                 240

Leu Ser Thr Leu Ser Glu Lys Ala Lys Pro Ala Leu Glu Asp Leu Arg
                245                 250                 255

Gln Gly Leu Leu Pro Val Leu Glu Ser Phe Lys Val Ser Phe Leu Ser
            260                 265                 270

Ala Leu Glu Glu Tyr Thr Lys Lys Leu Asn Thr Gln
        275                 280
```

<210> SEQ ID NO 2
<211> LENGTH: 291
<212> TYPE: PRT
<213> ORGANISM: Artificial Sequence
<220> FEATURE:
<223> OTHER INFORMATION: Tetranectin-apolipoprotein A-I with N-terminal
      His-tag
<220> FEATURE:
<221> NAME/KEY: MISC_FEATURE
<222> LOCATION: (7)..(7)
<223> OTHER INFORMATION: X = any one of AP, GP, SP, PP, GSAP, GSGP,
      GSSP, GSPP, GGGS, GGGGS, GGGSGGGS, GGGGSGGGGS, GGGSGGGSGGGS,
      GGGGSGGGGSGGGGS, GGGSAP, GGGSGP, GGGSSP
<220> FEATURE:
<221> NAME/KEY: MISC_FEATURE
<222> LOCATION: (7)..(7)
<223> OTHER INFORMATION: X = any one of GGGSPP, GGGGSAP, GGGGSGP,
      GGGGSSP, GGGGSPP, GGGSGGGSAP, GGGSGGGSGP, GGGSGGGSSP, GGGSGGGSPP,
      GGGSGGGSGGGSAP, GGGSGGGSGGGSGP, GGGSGGGSGGGSSP, GGGSGGGSGGGSPP <220> FEATURE:
<221> NAME/KEY: MISC_FEATURE
<222> LOCATION: (7)..(7)
<223> OTHER INFORMATION: X = any one of GGGGSAP, GGGGSGP, GGGGSSP,
    GGGGSPP, GGGGSGGGGSAP, GGGGSGGGGSGP, GGGGSGGGGSSP, GGGGSGGGGSPP,
    GGGGSGGGGSGGGGSAP, GGGGSGGGGSGGGGSGP, GGGGSGGGGSGGGGSSP, and
    GGGGSGGGGSGGGGSPP.
<220> FEATURE:
<221> NAME/KEY: misc_feature
<222> LOCATION: (8)..(8)
<223> OTHER INFORMATION: Xaa can be any naturally occurring amino acid

<400> SEQUENCE: 2

Met His His His His His Xaa Ile Val Asn Ala Lys Lys Asp Val
1               5                   10                  15

Val Asn Thr Lys Met Phe Glu Glu Leu Lys Ser Arg Leu Asp Thr Leu
            20                  25                  30

Ala Gln Glu Val Ala Leu Leu Lys Glu Gln Gln Ala Leu Gln Thr Val
        35                  40                  45

Asp Glu Pro Pro Gln Ser Pro Trp Asp Arg Val Lys Asp Leu Ala Thr
50                  55                  60

Val Tyr Val Asp Val Leu Lys Asp Ser Gly Arg Asp Tyr Val Ser Gln
65                  70                  75                  80

Phe Glu Gly Ser Ala Leu Gly Lys Gln Leu Asn Leu Lys Leu Leu Asp
                85                  90                  95

Asn Trp Asp Ser Val Thr Ser Thr Phe Ser Lys Leu Arg Glu Gln Leu
            100                 105                 110

Gly Pro Val Thr Gln Glu Phe Trp Asp Asn Leu Glu Lys Glu Thr Glu
        115                 120                 125

Gly Leu Arg Gln Glu Met Ser Lys Asp Leu Glu Glu Val Lys Ala Lys
    130                 135                 140

Val Gln Pro Tyr Leu Asp Asp Phe Gln Lys Lys Trp Gln Glu Glu Met
145                 150                 155                 160

Glu Leu Tyr Arg Gln Lys Val Glu Pro Leu Arg Ala Glu Leu Gln Glu
                165                 170                 175

Gly Ala Arg Gln Lys Leu His Glu Leu Gln Glu Lys Leu Ser Pro Leu
            180                 185                 190

Gly Glu Glu Met Arg Asp Arg Ala Arg Ala His Val Asp Ala Leu Arg
        195                 200                 205

Thr His Leu Ala Pro Tyr Ser Asp Glu Leu Arg Gln Arg Leu Ala Ala
    210                 215                 220

Arg Leu Glu Ala Leu Lys Glu Asn Gly Gly Ala Arg Leu Ala Glu Tyr
225                 230                 235                 240

His Ala Lys Ala Thr Glu His Leu Ser Thr Leu Ser Glu Lys Ala Lys
                245                 250                 255

Pro Ala Leu Glu Asp Leu Arg Gln Gly Leu Leu Pro Val Leu Glu Ser
            260                 265                 270

Phe Lys Val Ser Phe Leu Ser Ala Leu Glu Glu Tyr Thr Lys Lys Leu
        275                 280                 285

Asn Thr Gln
    290

<210> SEQ ID NO 3
<211> LENGTH: 285
<212> TYPE: PRT
<213> ORGANISM: Artificial Sequence
<220> FEATURE:
<223> OTHER INFORMATION: Tetranectin-apolipoprotein A-I (2)

<400> SEQUENCE: 3

Ala Pro Ile Val Asn Ala Lys Lys Asp Val Val Asn Thr Lys Met Phe
1               5                   10                  15

Glu Glu Leu Lys Ser Arg Leu Asp Thr Leu Ala Gln Glu Val Ala Leu
            20                  25                  30

Leu Lys Glu Gln Gln Ala Leu Gln Thr Val Asp Glu Pro Gln Ser
        35                  40                  45

Pro Trp Asp Arg Val Lys Asp Leu Ala Thr Val Tyr Val Asp Val Leu
    50                  55                  60

Lys Asp Ser Gly Arg Asp Tyr Val Ser Gln Phe Glu Gly Ser Ala Leu
65                  70                  75                  80

Gly Lys Gln Leu Asn Leu Lys Leu Leu Asp Asn Trp Asp Ser Val Thr
                85                  90                  95

Ser Thr Phe Ser Lys Leu Arg Glu Gln Leu Gly Pro Val Thr Gln Glu
                100                 105                 110

Phe Trp Asp Asn Leu Glu Lys Glu Thr Glu Gly Leu Arg Gln Glu Met
                115                 120                 125

Ser Lys Asp Leu Glu Glu Val Lys Ala Lys Val Gln Pro Tyr Leu Asp
130                 135                 140

Asp Phe Gln Lys Lys Trp Gln Glu Glu Met Glu Leu Tyr Arg Gln Lys
145                 150                 155                 160

Val Glu Pro Leu Arg Ala Glu Leu Gln Glu Gly Ala Arg Gln Lys Leu
                165                 170                 175

His Glu Leu Gln Glu Lys Leu Ser Pro Leu Gly Glu Glu Met Arg Asp
                180                 185                 190

Arg Ala Arg Ala His Val Asp Ala Leu Arg Thr His Leu Ala Pro Tyr
            195                 200                 205

Ser Asp Glu Leu Arg Gln Arg Leu Ala Ala Arg Leu Glu Ala Leu Lys
        210                 215                 220

Glu Asn Gly Gly Ala Arg Leu Ala Glu Tyr His Ala Lys Ala Thr Glu
225                 230                 235                 240

His Leu Ser Thr Leu Ser Glu Lys Ala Lys Pro Ala Leu Glu Asp Leu
                245                 250                 255

Arg Gln Gly Leu Leu Pro Val Leu Glu Ser Phe Lys Val Ser Phe Leu
                260                 265                 270

Ser Ala Leu Glu Glu Tyr Thr Lys Lys Leu Asn Thr Gln
            275                 280                 285

<210> SEQ ID NO 4
<211> LENGTH: 285
<212> TYPE: PRT
<213> ORGANISM: Artificial Sequence
<220> FEATURE:
<223> OTHER INFORMATION: Tetranectin-apolipoprotein A-I
<220> FEATURE:
<221> NAME/KEY: MISC_FEATURE
<223> OTHER INFORMATION: X = A or G or S or T
<220> FEATURE:
<221> NAME/KEY: misc_feature
<222> LOCATION: (1)..(1)
<223> OTHER INFORMATION: Xaa can be any naturally occurring amino acid

<400> SEQUENCE: 4

Xaa Pro Ile Val Asn Ala Lys Lys Asp Val Val Asn Thr Lys Met Phe
1               5                   10                  15

Glu Glu Leu Lys Ser Arg Leu Asp Thr Leu Ala Gln Glu Val Ala Leu
            20                  25                  30

-continued

```
Leu Lys Glu Gln Gln Ala Leu Gln Thr Val Asp Glu Pro Pro Gln Ser
        35                  40                  45

Pro Trp Asp Arg Val Lys Asp Leu Ala Thr Val Tyr Val Asp Val Leu
    50                  55                  60

Lys Asp Ser Gly Arg Asp Tyr Val Ser Gln Phe Glu Gly Ser Ala Leu
65                  70                  75                  80

Gly Lys Gln Leu Asn Leu Lys Leu Leu Asp Asn Trp Asp Ser Val Thr
                85                  90                  95

Ser Thr Phe Ser Lys Leu Arg Glu Gln Leu Gly Pro Val Thr Gln Glu
            100                 105                 110

Phe Trp Asp Asn Leu Glu Lys Glu Thr Glu Gly Leu Arg Gln Glu Met
        115                 120                 125

Ser Lys Asp Leu Glu Glu Val Lys Ala Lys Val Gln Pro Tyr Leu Asp
    130                 135                 140

Asp Phe Gln Lys Lys Trp Gln Glu Glu Met Glu Leu Tyr Arg Gln Lys
145                 150                 155                 160

Val Glu Pro Leu Arg Ala Glu Leu Gln Glu Gly Ala Arg Gln Lys Leu
                165                 170                 175

His Glu Leu Gln Glu Lys Leu Ser Pro Leu Gly Glu Glu Met Arg Asp
            180                 185                 190

Arg Ala Arg Ala His Val Asp Ala Leu Arg Thr His Leu Ala Pro Tyr
        195                 200                 205

Ser Asp Glu Leu Arg Gln Arg Leu Ala Ala Arg Leu Glu Ala Leu Lys
    210                 215                 220

Glu Asn Gly Gly Ala Arg Leu Ala Glu Tyr His Ala Lys Ala Thr Glu
225                 230                 235                 240

His Leu Ser Thr Leu Ser Glu Lys Ala Lys Pro Ala Leu Glu Asp Leu
                245                 250                 255

Arg Gln Gly Leu Leu Pro Val Leu Glu Ser Phe Lys Val Ser Phe Leu
            260                 265                 270

Ser Ala Leu Glu Glu Tyr Thr Lys Lys Leu Asn Thr Gln
        275                 280                 285
```

CATION AND ANION EXCHANGE CHROMATOGRAPHY METHOD

RELATED APPLICATION

This application is a continuation of U.S. patent application Ser. No. 13/588,281 filed Aug. 17, 2012, which claims the benefit of European Patent Application No. 11178745.3 filed Aug. 25, 2011 and European Patent Application No. 11183862.9 filed Oct. 4, 2011, which is fully incorporated herein by reference.

BACKGROUND OF THE INVENTION

Proteins play an important role in today's medical portfolio. Expression systems for the production of recombinant polypeptides are well-known in the state of the art. Polypeptides for use in pharmaceutical applications are mainly produced in prokaryotic cells, such as E. coli, and mammalian cells such as CHO cells, NS0 cells, Sp2/0 cells, COS cells, HEK cells, BHK cells, PER.C6® cells, and the like.

For human application every pharmaceutical substance has to meet distinct criteria. To ensure the safety of biopharmaceutical agents to humans, for example, nucleic acids, viruses, and host cell proteins, which would cause severe harm, have to be removed. To meet the regulatory specification one or more purification steps have to follow the manufacturing process. Among other, purity, throughput, and yield play an important role in determining an appropriate purification process.

Different methods are well established and widespread used for protein purification, such as affinity chromatography with microbial proteins (e.g. protein A or protein G affinity chromatography), ion exchange chromatography (e.g. cation exchange (sulfopropyl or carboxymethyl resins), anion exchange (amino ethyl resins) and mixed-mode ion exchange), thiophilic adsorption (e.g. with beta-mercaptoethanol and other SH ligands), hydrophobic interaction or aromatic adsorption chromatography (e.g. with phenyl-sepharose, aza-arenophilic resins, or m-aminophenylboronic acid), metal chelate affinity chromatography (e.g. with Ni(II)- and Cu(II)-affinity material), size exclusion chromatography, and electrophoretical methods (such as gel electrophoresis, capillary electrophoresis) (see e.g. Vijayalakshmi, M. A., Appl. Biochem. Biotech. 75 (1998) 93-102).

Necina, R., et al. (Biotechnol. Bioeng. 60 (1998) 689-698) reported the capture of human monoclonal antibodies directly from cell culture supernatants by ion exchange media exhibiting high charge density. In WO 89/05157 a method is reported for the purification of product immunoglobulins by directly subjecting the cell culture medium to a cation exchange treatment. A one-step purification of monoclonal IgG antibodies from mouse ascites is described by Danielsson, A., et al., J. Immun Meth. 115 (1988) 79-88. A method for purifying a polypeptide by ion exchange chromatography is reported in WO 2004/024866 in which a gradient wash is used to resolve a polypeptide of interest from one or more contaminants. In EP 0 530 447 a process for purifying IgG monoclonal antibodies by a combination of three chromatographic steps is reported. Wang, et al. (Wang, H., et al., Peptides 26 (2005) 1213-1218) reports the purification of hTFF3 expressed in E. coli by a two-step cation exchange chromatography.

In WO 2010/063717 polypeptide purification is reported. Protein purification and identification is reported in WO 2008/002235. Cole, D. R., reports the chromatography of insulin in urea-containing buffer (J. Biol. Chem. 235 (1960) 2294-2299. In U.S. Pat. No. 4,129,560 a process for the purification of high molecular weight peptides using non-ionic detergents is reported. A method for the preparation of growth hormone and antagonist thereof having lower levels of isoform impurities thereof is reported in WO 2004/031213. In U.S. Pat. No. 6,451,987 ion exchange chromatography of proteins and peptides is reported. A process for purifying insulin and insulin so prepared is reported in EP 0 013 826.

Herein is reported an ion exchange chromatography method for the purification of polypeptides by elution of the polypeptide from the ion chromatography material with a solution comprising a denaturant.

SUMMARY OF THE INVENTION

It has been found that a polypeptide can be recovered from an ion exchange chromatography material (cation and/or anion exchange chromatography material) with a solution comprising a denaturant/chaotropic agent, whereby during the recovering of the polypeptide from the ion exchange chromatography material the conductivity of the applied solutions is maintained constant, i.e. the conductivity is kept constant.

One aspect as reported herein is a method for obtaining or purifying a polypeptide by ion exchange chromatography in bind-and-elute mode comprising the following step:
  recovering the polypeptide from the ion exchange chromatography material by applying a solution comprising a denaturant and thereby obtaining or purifying the polypeptide,
whereby the ion exchange chromatography material comprises a matrix of cross-linked poly (styrene-divinylbenzene) to which ionic ligands have been attached.

In one embodiment the method comprises the following steps:
  recovering the polypeptide from a first ion exchange chromatography material by applying a solution comprising a denaturant,
  applying the recovered polypeptide to a second ion exchange chromatography material, and
  recovering the polypeptide from the second ion exchange chromatography material by applying a solution comprising a denaturant and thereby obtaining or purifying the polypeptide.

In one embodiment the first ion exchange chromatography material is an anion exchange chromatography material and the second ion exchange chromatography material is a cation exchange chromatography material.

In one embodiment the first ion exchange chromatography material is a cation exchange chromatography material and the second ion exchange chromatography material is an anion exchange chromatography material.

In one embodiment the denaturant is urea or a urea-derivative.

In one embodiment the denaturant is a mixture of two or three denaturants.

In one embodiment the solution applied in the recovering has a constant conductivity.

In one embodiment the solution applied in the wash step has a constant conductivity.

In one embodiment the solution applied in the recovering has a constant pH-value.

In one embodiment the solution applied in the wash step has a constant pH-value.

In one embodiment the method comprises the following steps:

applying a solution comprising the polypeptide in native form to an ion exchange chromatography material, and recovering the polypeptide from the ion exchange chromatography material by applying a solution comprising a denaturant and thereby obtaining or purifying the polypeptide.

In one embodiment the ion exchange chromatography material is a cation exchange chromatography material. In one embodiment the ligand is sulfopropyl or carboxymethyl.

In one embodiment the ion exchange chromatography material is an anion exchange chromatography material. In one embodiment the ligand is poly ethyleneimine or quaternized ethyleneimine.

In one embodiment the polypeptide is an antibody, or an antibody fragment, or a fusion polypeptide comprising at least one antibody domain.

In one embodiment the polypeptide is a tetranectin-apolipoprotein A-I fusion protein. In one embodiment the tetranectin-apolipoprotein A-I fusion protein has an amino acid sequence of SEQ ID NO: 01, or SEQ ID NO: 02, or SEQ ID NO: 03, or SEQ ID NO: 04.

One aspect as reported herein is a method for producing a polypeptide comprising the following steps:
cultivating a prokaryotic or eukaryotic cell comprising a nucleic acid encoding the polypeptide,
recovering the polypeptide from the cells or/and the cultivation medium,
if the polypeptide is recovered in the form of inclusion bodies solubilizing and/or re-folding the polypeptide,
purifying the polypeptide with an ion exchange chromatography method as reported herein and thereby producing the polypeptide.

DETAILED DESCRIPTION OF THE INVENTION

Figure 1:
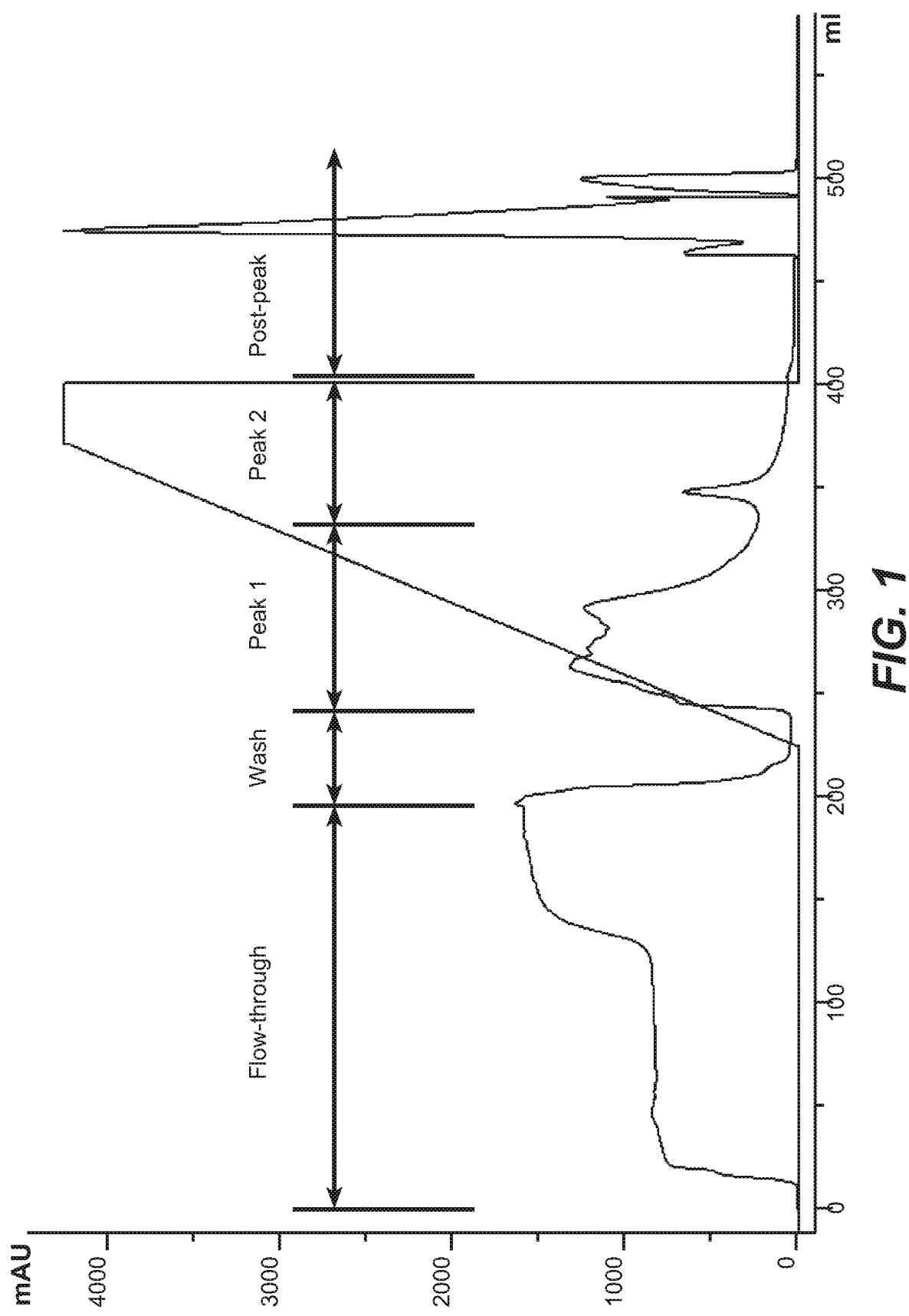
FIG. 1 Chromatogram of a purification of tetranectin-apolipoprotein A-I fusion protein of SEQ ID NO: 01 on an anion exchange chromatography column with sodium chloride conductivity gradient.

Herein is reported a scalable ion exchange chromatography method operated in bind-and-elute mode for the purification of polypeptides wherein the recovering of the polypeptide from the ion exchange chromatography material is with a solution comprising a denaturant, wherein the conductivity of the solution used in the recovering step is maintained constant.

The terms "applying to" and grammatical equivalents thereof denote a partial step of a purification method in which a solution containing a substance of interest to be purified is brought in contact with a stationary phase. This denotes that a) the solution is added to a chromatographic device in which the stationary phase is located, or b) that a stationary phase is added to the solution comprising the substance of interest. In case a) the solution containing the substance of interest to be purified passes through the stationary phase allowing for an interaction between the stationary phase and the substances in solution. Depending on the conditions, such as e.g. pH, conductivity, salt concentration, temperature, and/or flow rate, some substances of the solution are bound to the stationary phase and, thus, are removed from the solution. Other substances remain in solution. The substances remaining in solution can be found in the flow-through. The "flow-through" denotes the solution obtained after the passage of the chromatographic device irrespective of its origin. It can either be the applied solution containing the substance of interest or the buffer, which is used to flush the column or which is used to cause the elution of one or more substances bound to the stationary phase. In one embodiment the chromatographic device is a column, or a cassette. The substance of interest can be recovered from the solution after the purification step by methods familiar to a person of skill in the art, such as e.g. precipitation, salting out, ultrafiltration, diafiltration, lyophilization, affinity chromatography, or solvent volume reduction to obtain the substance of interest in purified or even substantially homogeneous form. In case b) the stationary phase is added, e.g. as a solid, to the solution containing the substance of interest to be purified allowing for an interaction between the stationary phase and the substances in solution. After the interaction the stationary phase is removed, e.g. by filtration, and the substance of interest is either bound to the stationary phase and removed therewith from the solution or the substance of interest is not bound to the stationary phase and remains in the solution.

The term "buffered" as used within this application denotes a solution in which changes of pH due to the addition or release of acidic or basic substances is leveled by a buffer substance. Any buffer substance resulting in such an effect can be used. In one embodiment the buffer substance is selected from phosphoric acid or salts thereof, acetic acid or salts thereof, citric acid or salts thereof, morpholine, 2-(N-morpholino) ethanesulfonic acid or salts thereof, imidazole or salts thereof, histidine or salts thereof, glycine or salts thereof, or tris (hydroxymethyl) aminomethane (TRIS) or salts thereof. In one embodiment the buffer substance is selected from imidazole or salt thereof or histidine or salts thereof. Optionally the buffered solution may also comprise an additional inorganic salt. In one embodiment the inorganic salt is selected from sodium chloride, sodium sulphate, potassium chloride, potassium sulfate, sodium citrate, and potassium citrate.

A "polypeptide" is a polymer consisting of amino acids joined by peptide bonds, whether produced naturally or synthetically. Polypeptides of less than about 20 amino acid residues may be referred to as "peptides", whereas molecules consisting of two or more polypeptides or comprising one polypeptide of more than 100 amino acid residues may be referred to as "proteins". A polypeptide may also comprise non-amino acid components, such as carbohydrate groups, metal ions, or carboxylic acid esters. The non-amino acid components may be added by the cell, in which the polypeptide is expressed, and may vary with the type of cell. Polypeptides are defined herein in terms of their amino acid backbone structure or the nucleic acid encoding the same. Additions such as carbohydrate groups are generally not specified, but may be present nonetheless.

The term "antibody" denotes a protein that comprises at least two light polypeptide chains and two heavy polypeptide chains. Each of the heavy and light polypeptide chains contains a variable region (generally the amino terminal portion of the polypeptide chain) which contains a binding domain for interaction with the antigen. Each of the heavy and light polypeptide chains also comprises a constant region (generally the carboxyl terminal portion) which may mediate the binding of the antibody to host tissues or factors including various cells of the immune system, some phagocytic cells and a first component (C1q) of the classical complement system. Typically, the light and heavy polypeptide chains are complete chains, each consisting essentially of a variable region, i.e. $V_L$ or $V_H$, and a complete constant region, i.e. of $C_L$ in case of a light polypeptide chain or of $C_H1$, $C_H2$, $C_H3$, and optionally $C_H4$ in case of a heavy polypeptide chain. The variable regions of the antibody according to the invention can be grafted to constant regions of other isotypes. For example, a polynucleotide encoding the variable region of a heavy chain of the 1-isotype can be grafted to polynucleotide encoding the constant region of another heavy chain class (or subclass).

Antibodies may exist in a variety of forms, including, for example, Fv, Fab, and F(ab)$_2$ as well as single chains (e.g. Huston, J. S., et al., Proc. Natl. Acad. Sci. USA 85 (1988) 5879-5883; Bird, R. E., et al., Science 242 (1988) 423-426; and, in general, Hood, R et al., Immunology, Benjamin N.Y., 2nd edition, The Benjamin/Cummings Publishing Company, Inc. (1984), and Hunkapiller, T. and Hood, L., Nature 323 (1986) 15-16). In one embodiment the antibody is selected from monoclonal antibody, isolated heavy or light chain, or heavy or light chains only consisting of constant regions as well as fragments thereof.

The term "constant" denotes that a certain value is maintained at a level with a relative change of at most 10%. In one embodiment the conductivity of the solution in the recovering step is maintained constant with a change of at most+/−10%. In one embodiment the conductivity of the solution in the recovering step is maintained constant with a change of at most+/−5%. In one embodiment the conductivity of the solution in the recovering step is maintained constant with a change of at most+/−2%.

The term "bind-and-elute mode" denotes a way to perform a chromatography purification method. Herein a solution containing a polypeptide of interest to be purified is applied to a stationary phase, particularly a solid phase, whereby the polypeptide of interest interacts with the stationary phase and is retained thereon. Substances not of interest are removed with the flow-through or the supernatant, respectively. The polypeptide of interest is afterwards recovered from the stationary phase in a second step by applying an elution solution.

The term "inclusion body" denotes a dense intracellular mass of aggregated polypeptide of interest, which constitutes a significant portion of the total cell protein, including all cell components of a prokaryotic cell.

The term "denaturized" denotes forms of polypeptides wherein these have a secondary, tertiary, and/or quaternary structure that is not the native one. The polypeptide in this non-native form may be soluble but concomitantly in a biologically inactive conformation. Or the polypeptide may be insoluble and in a biologically inactive conformation with e.g. mismatched or unformed disulfide bonds. This insoluble polypeptide can be, but need not be, contained in inclusion bodies.

The term "refolded" refers to a polypeptide obtained from a denaturized form. Typically, the goal of refolding is to produce a protein having a higher level of activity than the protein would have if produced without a refolding step. A folded protein molecule is most stable in the conformation that has the least free energy. Most water soluble proteins fold in a way that most of the hydrophobic amino acids are in the interior part of the molecule, away from water. The weak bonds that hold a protein together can be disrupted by a number of treatments that cause a polypeptide to unfold, i.e. to denaturize. A folded protein is the product of several types of interactions between the amino acids themselves and their environment, including ionic bonds, Van der Waals interactions, hydrogen bonds, disulfide bonds and covalent bonds.

The terms "denatured" or "denaturized" as used herein refer to a polypeptide in which ionic and covalent bonds and Van der Waals interactions which exist in the molecule in its native or refolded state are disrupted. Denaturation of a polypeptide can be accomplished, for example, by treatment with 8 M urea, reducing agents such as mercaptoethanol, heat, pH, temperature and other chemicals. Reagents such as 8 M urea disrupt both the hydrogen bonds and the hydrophobic bonds, and if mercaptoethanol is also added, the disulfide bridges (S—S) which are formed between cysteines are reduced to two —S—H groups. Refolding of polypeptides which contain disulfide linkages in their native or refolded state may also involve the oxidation of the —S—H groups present on cysteine residues for the protein to reform the disulfide bonds.

The term "chaotropic agent" or "denaturant", which can be used interchangeably, denotes a compound that distorts the three-dimensional structure of a polypeptide. This process is also called denaturation. The chaotropic agent distorts/disrupts interactions by non-covalent forces such as hydrogen bonds, or van der Waals forces. In one embodiment the chaotropic agent is selected from the group comprising butanol, ethanol, 1- and 2-propanol, guanidinium chloride, magnesium chloride, sodium dodecyl/sodium lauryl sulfate, urea, and thiourea.

The term "in native form" denotes the form of a polypeptide wherein it has a secondary, tertiary, and/or quaternary structure in which the polypeptide has his biological activity.

The term "ion exchange chromatography material" denotes an immobile high molecular weight matrix that carries covalently bound charged substituents. For overall charge neutrality not covalently bound counter ions are bound to the charged substituents by ionic interaction. The "ion exchange chromatography material" has the ability to exchange its not covalently bound counter ions for similarly charged binding partners or ions of the surrounding solution. Depending on the charge of its exchangeable counter ions the "ion exchange chromatography material" is referred to as "cation exchange chromatography material" or as "anion exchange chromatography material". Depending on the nature of the charged group (substituent) the "ion exchange chromatography material" is referred to as, e.g. in the case of cation exchange materials, sulfonic acid or sulfopropyl resin (S), or carboxymethyl resin (CM). Depending on the chemical nature of the charged group/substituent the "ion exchange chromatography material" can additionally be classified as strong or weak ion exchange material, depending on the strength of the covalently bound charged substituent. For example, strong cation exchange materials have a sulfonic acid group, such as a sulfopropyl group, as charged substituent, weak cation exchange materials have a carboxylic acid group, such as a carboxymethyl group, as charged substituent. Strong anion exchange materials have a quarternary ammonium group, and weak anion exchange materials have a diethylaminoethyl group as charged substituent.

Generally, the position of an ion exchange chromatography step is variable in a multi-step purification sequence of a polypeptide.

Methods for purifying polypeptides are well established and widespread used. They are employed either alone or in combination. Such methods are, for example, affinity chromatography using thiol ligands with complexed metal ions (e.g. with Ni(II)- and Cu(II)-affinity material) or microbial-derived proteins (e.g. protein A or protein G affinity chromatography), ion exchange chromatography (e.g. cation exchange (carboxymethyl resins), anion exchange (amino ethyl resins) and mixed-mode exchange chromatography), thiophilic adsorption (e.g. with beta-mercaptoethanol and other SH ligands), hydrophobic interaction or aromatic adsorption chromatography (e.g. with phenyl-sepharose, aza-arenophilic resins, or m-aminophenylboronic acid), size exclusion chromatography, and preparative electrophoretic methods (such as gel electrophoresis, capillary electrophoresis).

The purification process of immunoglobulins in general comprises a multistep chromatographic part. In the first step non-immunoglobulin polypeptides and proteins are separated from the immunoglobulin fraction by an affinity chromatography, e.g. with protein A. Afterwards an ion exchange chromatography can be performed. Finally a third chromatographic step can be performed to separate immunoglobulin monomers from multimers and fragments of the same class. Sometimes the amount of aggregates is high (5% or more) and it is not possible to separate them efficiently in the third purification step necessitating further purification steps.

It has been found that a polypeptide can be recovered from an ion exchange chromatography material, which comprises a matrix of cross-linked poly (styrene-divinylbenzene) to which ionic ligands have been attached, with a solution comprising a denaturant, whereby the conductivity of the solution is kept constant during the recovering. This finding was very surprising as generally an increase in ionic strength is used to recover polypeptides from ion exchange chromatography materials. At the same time this chromatography material has sufficient binding capacity for industrial production scale separations.

Therefore, one aspect as reported herein is a method for obtaining or purifying a polypeptide comprising the following step:
  recovering the polypeptide from an ion exchange chromatography material by applying a solution comprising a denaturant and thereby obtaining or purifying the polypeptide,
whereby the ion exchange chromatography material comprises a matrix of cross-linked poly (styrene-divinylbenzene) to which ionic ligands have been attached.

As a denaturant is used for the recovery of the bound polypeptide the solution comprising the polypeptide which is applied to the ion exchange chromatography material is free of denaturants. The polypeptide retained on the ion exchange chromatography material is recovered with a solution comprising a denaturant such as urea or a urea-derivative and a constant conductivity.

The method as reported herein is, thus, operated in bind-and-elute mode, i.e. the polypeptide is first bound to the ion exchange chromatography material and thereafter, in a further step, recovered from the ion exchange chromatography material. Intermittent wash steps can be included in the methods as reported herein. In these wash steps the applied solution(s) is (are) substantially free of a denaturant. The term "substantially free of a denaturant" denotes that a denaturant can be present in the applied (wash) solution but at a concentration that is below the concentration required for the recovery of the polypeptide from the ion exchange material.

In the method as reported herein all solutions are free of, i.e. do not contain, a denaturant except for the solution for recovering the polypeptide from the ion exchange chromatography material. In one embodiment the solution comprising the denaturant is an aqueous solution. In a further embodiment the solution comprising the denaturant does not comprise, i.e. it is free of, an organic solvent and/or an aliphatic alcohol. In a further embodiment the solution comprising the denaturant is consisting of water, the denaturant, a buffer substance, and optionally one or two or three inorganic salts.

The term "denaturant" or "chaotropic agent", which can be used interchangeably within this application, denotes compounds that transfer a polypeptide from its native form in a non-native, i.e. denatured, form. Denaturants are generally chaotropic agents. Exemplary denaturants are urea and urea-derivatives, guanidine and guanidine-derivatives, tetraalkyl ammonium salts, long chain sulfonic acid esters, and lithium perchlorate.

The addition of urea, to be more precise, the change of the concentration of urea does not affect the conductivity of a solution, i.e. the conductivity of a solution remains constant upon the addition or change of the concentration of urea.

In one embodiment the denaturant is urea or a urea-derivative.

In one embodiment the denaturant is urea. In one embodiment the urea has a concentration of from 4 mol/l to 9 mol/l.

In one embodiment the denaturant is thiourea. In one embodiment the thiourea has a concentration of from 1.5 mol/l to 3 mol/l.

In one embodiment the denaturant is a mixture of two or three denaturants. In one embodiment the denaturant is a mixture of urea and thiourea. In one embodiment the denaturant is a mixture of urea and a guanidinium salt.

In one embodiment of the aspects as reported herein the method for purifying or obtaining a polypeptide comprises the following steps:
- applying a first solution to the ion exchange chromatography material to produce a conditioned ion exchange chromatography material,
- applying a second solution comprising the polypeptide to the conditioned ion exchange chromatography material,
- optionally applying a third solution to the ion exchange chromatography material,
- recovering and thereby purifying or obtaining the polypeptide with a fourth solution comprising a denaturant from the ion exchange chromatography material.

The first and second solutions are substantially free of a denaturant. The third solution is substantially free of a denaturant.

Polypeptides can be produced recombinantly in eukaryotic and prokaryotic cells, such as CHO cells, HEK cells and *E. coli*. If the polypeptide is produced in prokaryotic cells it is generally obtained in the form of insoluble inclusion bodies. The inclusion bodies can easily be recovered from the prokaryotic cell and the cultivation medium. The polypeptide obtained in insoluble form in the inclusion bodies has to be solubilized before purification and/or re-folding procedure can be carried out.

Thus, a second aspect as reported herein is a method for producing a polypeptide comprising the following steps:
- cultivating a prokaryotic or eukaryotic cell comprising a nucleic acid encoding the polypeptide,
- recovering the polypeptide from the prokaryotic or eukaryotic cells or/and the cultivation medium,
- optionally if the polypeptide is recovered in form of inclusion bodies solubilizing and/or re-folding the polypeptide,
- purifying the polypeptide with an ion exchange chromatography method as reported herein and thereby producing a polypeptide.

In one embodiment the ion exchange chromatography method comprises the following steps:
- applying a first solution to the ion exchange chromatography material to produce a conditioned ion exchange chromatography material,
- applying a second solution comprising the polypeptide to the conditioned ion exchange chromatography material,
- optionally applying a third solution (wash step) to the ion exchange chromatography material,
- recovering and thereby producing the polypeptide with a fourth solution comprising one or more denaturants from the ion exchange chromatography material,
whereby the first to third solutions are free of denaturants.

In the following different embodiments of all the aspects as reported before are presented.

In one embodiment the first solution comprises a first buffer substance, the second solution comprises a second buffer substance, the third solution comprises a third buffer substance, and the fourth solution comprises a fourth buffer substance, whereby the fourth buffer substance comprises one or more denaturants.

In one embodiment the second buffer substance and the third buffer substance and the fourth buffer substance are all different buffer substances.

In one embodiment the first solution and/or the second solution and/or the third solution is/are free of a denaturant. In one embodiment the third solution is substantially free of a denaturant.

In one embodiment the applying of the first solution is for 3 to 20 column volumes. In one embodiment the applying of the first solution is for 3 to 10 column volumes.

In one embodiment the applying of the second solution is for 1 to 10 column volumes.

In one embodiment the applying of the third solution is for 1 to 10 column volumes.

The ion exchange chromatography material is in the first step conditioned with a buffered solution. This solution is free of, i.e. does not comprise, a denaturant. The buffer substance of the conditioning, first buffer solution can be the same or different from the buffer substance of the second solution comprising the polypeptide.

Thereafter a second solution comprising the polypeptide is applied to the conditioned ion exchange chromatography material. In this step the polypeptide is retained on the ion exchange chromatography material. This solution does not comprise a denaturant. The buffer substance of the loading, i.e. second, buffer solution can be the same or different from the buffer substance of the third solution.

After the loading of the ion exchange chromatography material with the polypeptide optionally a washing, i.e. third, solution can be applied to the loaded ion exchange chromatography material. This solution is substantially free of a denaturant.

Finally for recovering the polypeptide from the ion exchange chromatography material a recovering, i.e. fourth, solution comprising one or more denaturants is applied to the chromatography material.

In one embodiment the method for purifying or obtaining a polypeptide is a column chromatography method.

In one embodiment the conductivity of the solution in the recovering step is constant.

In one embodiment the pH-value of the solution in the recovering step is constant.

The volume applied to the ion exchange chromatography material in the different steps is independently of each other of from 3 to 20 column volumes, in one embodiment of from 4 to 10 column volumes.

In one embodiment the ion exchange chromatography material is made of polystyrene divinyl benzene derivatized with functional groups. In one embodiment the anion exchange chromatography material is a polystyrene divinyl benzene derivatized with quaternized poly ethyleneimine functional groups. In one embodiment the cation exchange chromatography material is a polystyrene divinyl benzene derivatized with sulfopropyl functional groups.

The methods as reported herein are exemplified in the following with a tetranectin-apolipoprotein A-I fusion protein as reported in WO 2012/028526 and an anti-TSLP receptor antibody as reported in WO 2012/007495.

The following examples and figures are provided to aid the understanding of the present invention, the true scope of which is set forth in the appended claims. It is understood that modifications can be made in the procedures set forth without departing from the spirit of the invention.

EXAMPLE 1

Material and Methods

If not otherwise indicated the different chromatography methods have been performed according to the chromatography material manufacturer's manual.

Recombinant DNA Techniques

Standard methods were used to manipulate DNA as described in Sambrook, J., et al., Molecular Cloning: A Laboratory Manual; Cold Spring Harbor Laboratory Press, Cold Spring Harbor, N.Y. (1989). The molecular biological reagents were used according to the manufacturer's instructions.

Protein Determination

Protein concentration was determined by determining the optical density (OD) at 280 nm, with a reference wavelength of 320 nm, using the molar extinction coefficient calculated on the basis of the amino acid sequence.

Size-Exclusion-HPLC

The chromatography was conducted with a Tosoh Haas TSK 3000 SWXL column on an ASI-100 HPLC system (Dionex, Idstein, Germany). The elution peaks were monitored at 280 nm by a UV diode array detector (Dionex). After dissolution of the concentrated samples to 1 mg/ml the column was washed with a buffer consisting of 200 mM potassium dihydrogen phosphate and 250 mM potassium chloride pH 7.0 until a stable baseline was achieved. The analyzing runs were performed under isocratic conditions using a flow rate of 0.5 ml/min. over 30 min. at room temperature. The chromatograms were integrated manually with Chromeleon (Dionex, Idstein, Germany).

Reversed Phase HPLC (RP-HPLC)

The purity is analyzed by RP-HPLC. The assay is performed on a Phenomenex C18 column using an acetonitrile/aqueous TFA gradient. The elution profile is monitored as UV absorbance at 215 nm. The percentages of the eluted substances are calculated based upon the total peak area of the eluted proteins.

DNA-Threshold-System

See e.g. Merrick, H., and Hawlitschek, G., Biotech Forum Europe 9 (1992) 398-403.

Host Cell Protein Determination

The walls of the wells of a micro titer plate are coated with a mixture of serum albumin and Streptavidin. A goat derived polyclonal antibody against HCP is bound to the walls of the wells of the micro titer plate. After a washing step different wells of the micro titer plate are incubated with a HCP calibration sequence of different concentrations and sample solution. After the incubation not bound sample material is removed by washing with buffer solution. For the detection the wells are incubated with an antibody peroxidase conjugate to detect bound host cell protein. The fixed peroxidase activity is detected by incubation with ABTS and detection at 405 nm.

DNA Determination

Biotin was bound to a microtiter plate. A reaction mixture of streptavidin, single-stranded DNA and biotinylated single-stranded DNA binding protein was added. The binding protein was able to bind DNA and was biotinylated. In this manner it was possible to specifically remove the DNA from the sample mixture. The streptavidin bound the biotin on the microtiter plate as well as the biotin which was coupled to the single-stranded DNA binding protein. A DNA-specific antibody which was coupled to urease was added to this total complex. Addition of urea resulted in a hydrolysis of the urea which caused a local change in the pH. This change can be detected as an altered surface potential. The change in the surface potential was proportional to the amount of bound DNA. Single stranded DNA was obtained by proteinase K digestion and denaturation with SDS.

General Method for the Isolation, Solubilization and Re-Folding of Polypeptide from Inclusion Bodies In addition to the method performed in the cited literature can the preparation of inclusion bodies e.g. be performed according the method by Rudolph, et al. (Rudolph, R., et al., Folding Proteins, In: Creighton, T. E., (ed.): Protein function: A Practical Approach, Oxford University Press (1997) 57-99). The inclusion bodies were stored at −70° C. Solubilization of the inclusion bodies can likewise be performed according the method by Rudolph, et al. (Rudolph, R., et al., Folding Proteins, In: Creighton, T. E., (ed.): Protein function: A Practical Approach, Oxford University Press (1997) 57-99).

EXAMPLE 2

Comparative Example

Purification of Tetranectin-Apolipoprotein A-I Fusion Protein of SEQ ID NO: 01 on an Anion Exchange Chromatography Column with Sodium Chloride Conductivity Gradient resin: POROS® HQ
load: 443 mg polypeptide
column load: 30 mg/ml
elution method: linear gradient 0 M to 1 M sodium chloride
Result:
As can be seen from FIG. 1 the fusion protein cannot be obtained in a defined peak. The analytical results are shown in the following Table.

TABLE

|  | DNA [pg/mg] | ECP [ng/ml] | LAL [EU/ml] | c (fusion protein) [mg/ml] | yield [%] |
|---|---|---|---|---|---|
| applied solution | 1210000 | 4844100 | 21845 | 2.4 |  |
| flow through | <495458 | 35500 | 827 | 1.2 |  |
| wash | <37337 | 79950 | 549 | 1.6 |  |
| peak 1 | <2999 | 482490 | 21856 | 2.0 | 44.7 |
| peak 2 | <26786 | 79850 | 19573 | 0.2 | 3.3 |
| post peak | 23981818 | 35000 | 17476 | 0.1 |  |

EXAMPLE 3

Figure 2:
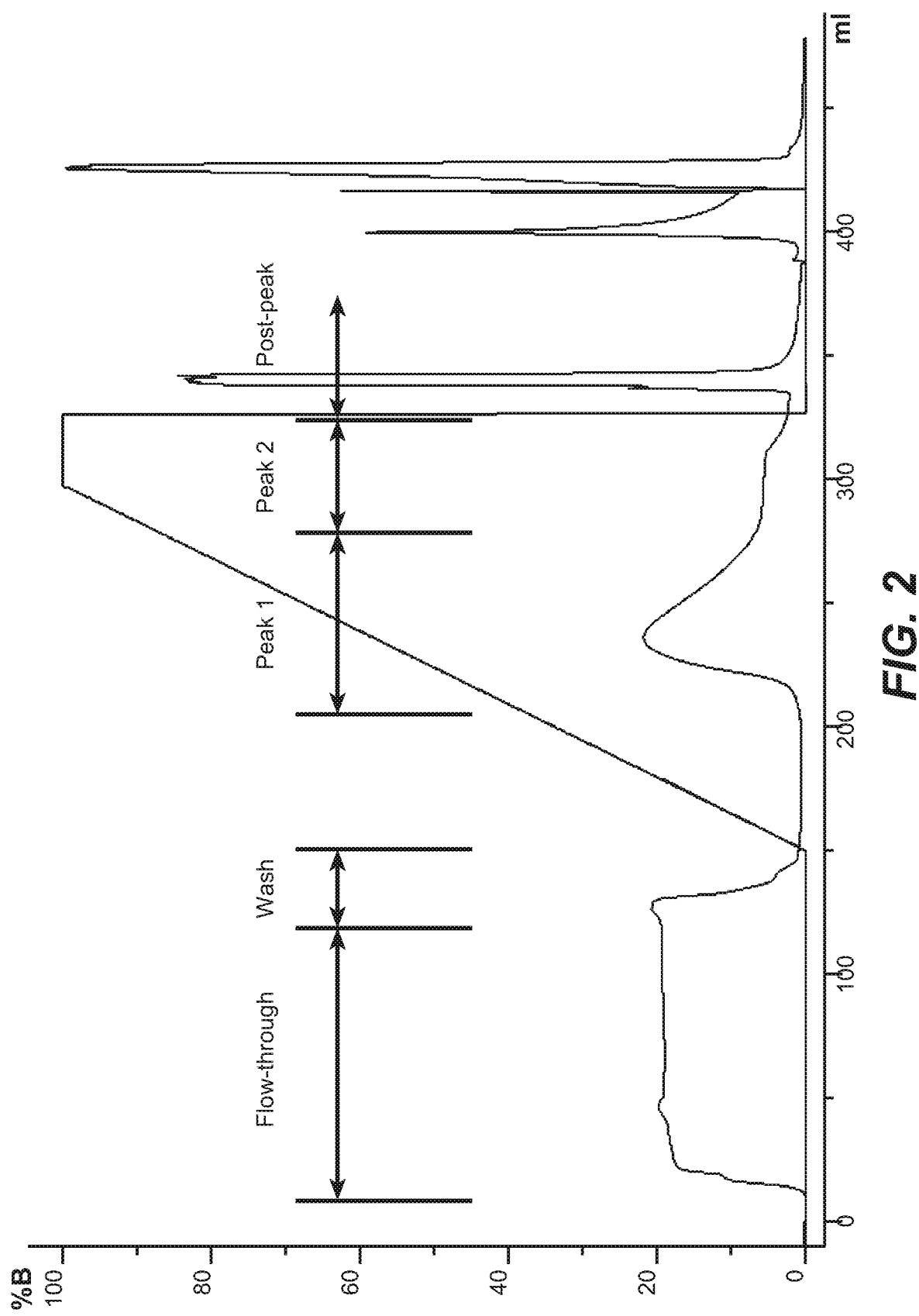
FIG. 2 Chromatogram of a purification of tetranectin-apolipoprotein A-I fusion protein of SEQ ID NO: 01 on an anion exchange chromatography column with urea gradient at constant conductivity and constant pH-value.

Purification of Tetranectin-Apolipoprotein A-I Fusion Protein of SEQ ID NO: 01 on an Anion Exchange Chromatography Column with Urea Gradient at Constant Conductivity and Constant pH-Value resin: POROS® HQ
load: 366 mg polypeptide
column load: 24.8 mg/ml
elution method: linear gradient 0 M to 6 M urea Result:

As can be seen from FIG. 2 the fusion protein can be obtained in a defined peak. The analytical results are shown in the following Table.

TABLE

|  | DNA [pg/mg] | ECP [ng/ml] | LAL [EU/ml] | c (fusion protein) [mg/ml] | yield [%] |
| --- | --- | --- | --- | --- | --- |
| applied solution | 989196 | 732700 | 9099 | 3.3 |  |
| flow through | <60000 | 11933 | 53 | 0 |  |
| wash | <2400000 | 8153 | 140 | 0.03 |  |
| peak 1 | <28860 | 4999 | 44 | 2.1 | 56.2 |
| peak 2 | <62959 | 3424 | 20 | 1.0 | 9.4 |
| post peak | <78431 | 83300 | 2089 | 0.8 |  |

EXAMPLE 4

Figure 3:
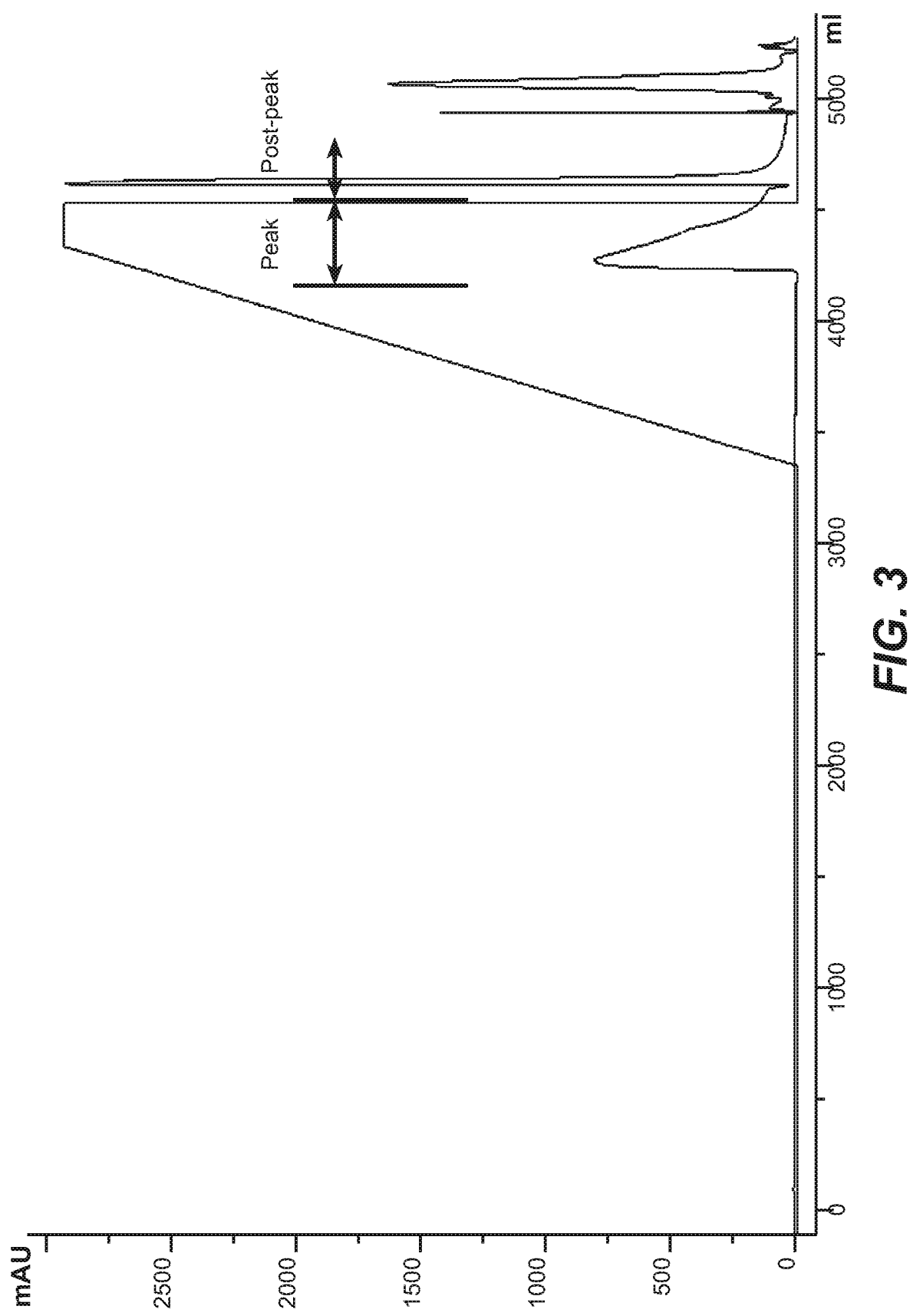
FIG. 3 Chromatogram of a purification of tetranectin-apolipoprotein A-I fusion protein of SEQ ID NO: 02 on an anion exchange chromatography column with urea gradient at constant conductivity and constant pH-value.

Purification of Tetranectin-Apolipoprotein A-I Fusion Protein of SEQ ID NO: 02 on an Anion Exchange Chromatography Column with Urea Gradient at Constant Conductivity and Constant pH-Value resin: POROS® HQ
elution method: linear gradient 0 M to 6 M urea
Result:

As can be seen from FIG. 3 the fusion protein can be obtained in a defined peak. The analytical results are shown in the following Table.

TABLE

|  | DNA [pg/mg] | ECP [ng/ml] | LAL [EU/ml] | c (fusion protein) [mg/ml] | yield [%] |
| --- | --- | --- | --- | --- | --- |
| applied solution | 8025 | 247340 | 1565 | 2.3 |  |
| peak 1 | <2.2 | 137 | <3 | 2.3 | 54.0 |
| post peak | 11144 | 24420 | 198 | 1.2 |  |

EXAMPLE 5

Comparative Example

Figure 4:
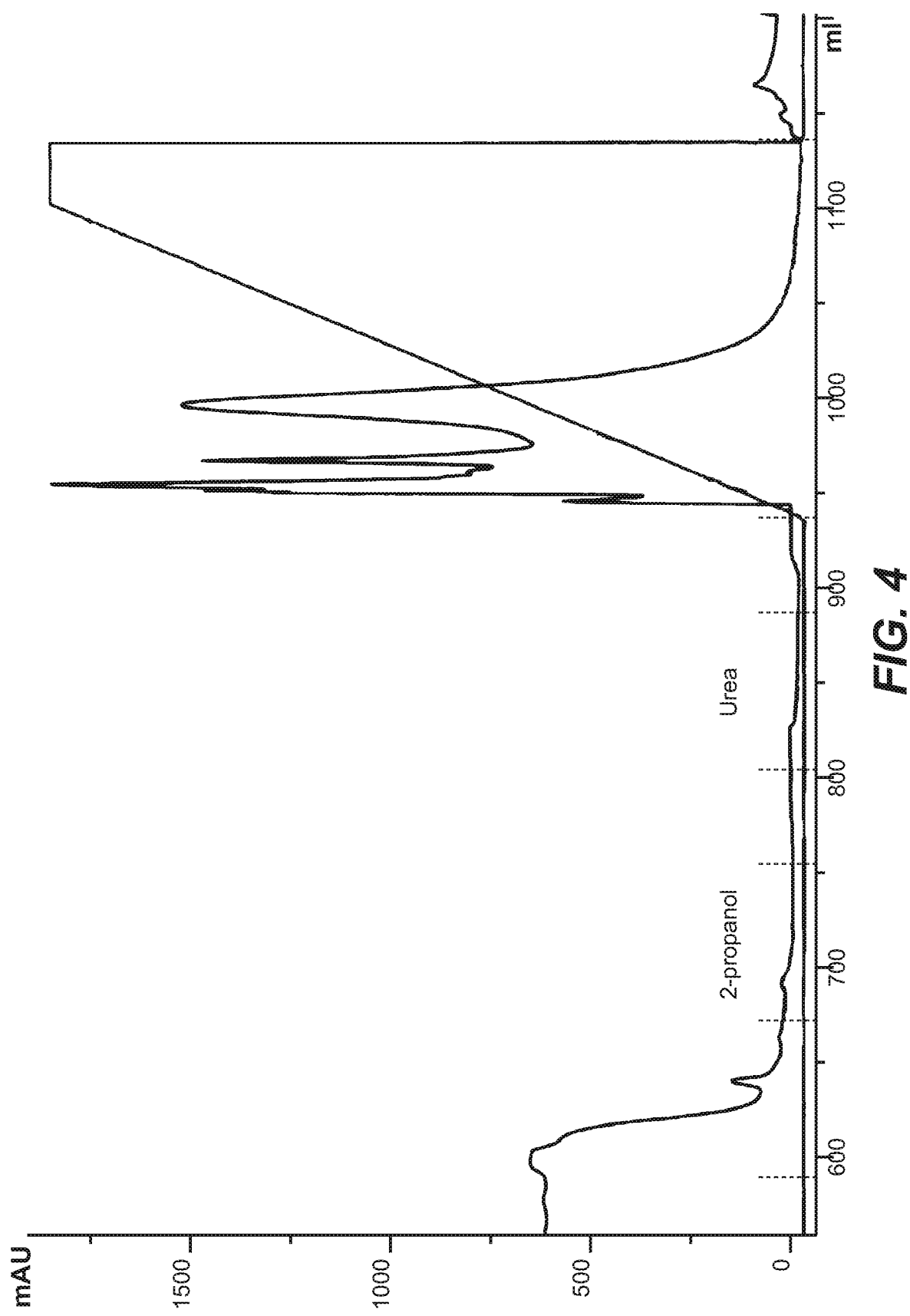
FIG. 4 Chromatogram of a purification of tetranectin-apolipoprotein A-I fusion protein of SEQ ID NO: 01 on an anion exchange chromatography column with urea wash, isopropanol wash and guanidinium hydrochloride gradient elution.

Purification of Tetranectin-Apolipoprotein A-I Fusion Protein of SEQ ID NO: 01 on an Anion Exchange Chromatography Column with Urea Wash, Isopropanol Wash and Guanidinium Hydrochloride Gradient Elution resin: Q-Sepharose® FF (GE Healthcare)
load: 281 mg polypeptide
column load: 15 mg/ml
equilibration: 30 mM potassium phosphate buffer pH 8.0; 5.94 mS/cm
urea wash: 6 M urea solution pH 8.0; 435 µS/cm
2-propanol wash: 20% (v/v) 2-propanol
elution solution: 6 M guanidinium hydrochloride pH 8.0; LF=278 mS/cm
wash steps:
  wash with 5 column volumes 6 M urea solution;
  wash with 5 column volumes 20% 2-propanol
elution method: linear gradient 0 M to 6 M guanidinium hydrochloride in 10 column volumes Result:

As can be seen from FIG. 4 the fusion protein cannot be obtained during the wash steps with the urea solution and the 2-propanol solution. Elution can only be effected by using the guanidinium hydrochloride solution.

EXAMPLE 6

Comparative Example

Figure 5:
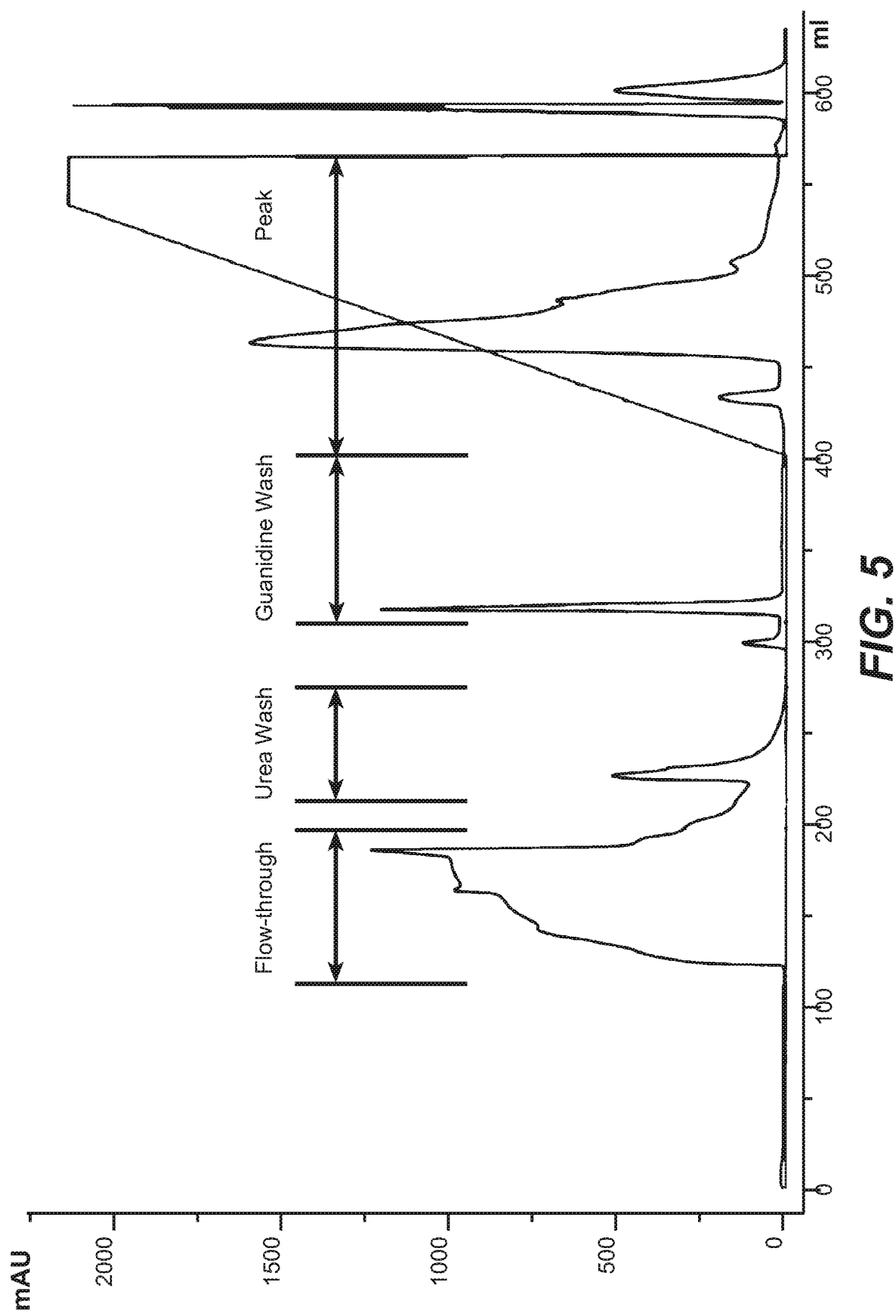
FIG. 5 Chromatogram of a purification of tetranectin-apolipoprotein A-I fusion protein of SEQ ID NO: 01 on an anion exchange chromatography column with urea wash, guanidinium hydrochloride wash and sodium chloride gradient elution.

Purification of Tetranectin-Apolipoprotein A-I Fusion Protein of SEQ ID NO: 01 on an Anion Exchange Chromatography Column with Urea Wash, Guanidinium Hydrochloride Wash and Sodium Chloride Gradient Elution resin: Q-Sepharose® FF (GE Healthcare)
load: 280 mg polypeptide
column load: 20 mg/ml
equilibration: 30 mM potassium phosphate buffer pH 8.0; 5.9 mS/cm
urea wash: 6 M urea solution pH 8.0; 435 µS/cm
guanidinium hydrochloride solution: 0.1 M guanidinium hydrochloride pH 8.0
elution solution: 1 M sodium chloride in 50 mM potassium phosphate buffer pH 8.0; 91.7 mS/cm
wash steps:
  wash with 5 column volumes 6 M urea solution;
  wash with 5 column volumes 0.1 M guanidinium hydrochloride solution
elution method: linear gradient 0 M to 1 M sodium chloride in 10 column volumes Result:

As can be seen from FIG. 5 that in each of the wash steps only a minor fraction of the fusion protein can be obtained. The analytical results are shown in the following Table.

TABLE

|  | DNA [pg/mg] | ECP [ng/ml] | LAL [EU/ml] | c (fusion protein) [mg/ml] | yield [%] |
| --- | --- | --- | --- | --- | --- |
| applied solution | 1210000 | 4844100 | 21845 | 4.0 |  |
| flow through | 88000 | 379270 | 4572 | n.d. |  |
| urea wash | 69700 | 22220 | 286 | n.d. |  |
| guanidinium wash | 2330 | 30810 | 1229 | n.d. |  |
| peak 1 | 117 | 308650 | 23484 | 4.3 | 37.7 |
| peak 2 | 19040 | 139645 | 6827 | 1.3 | 13.3 | n.d. = not determined

EXAMPLE 7

Comparative Example

Figure 6:
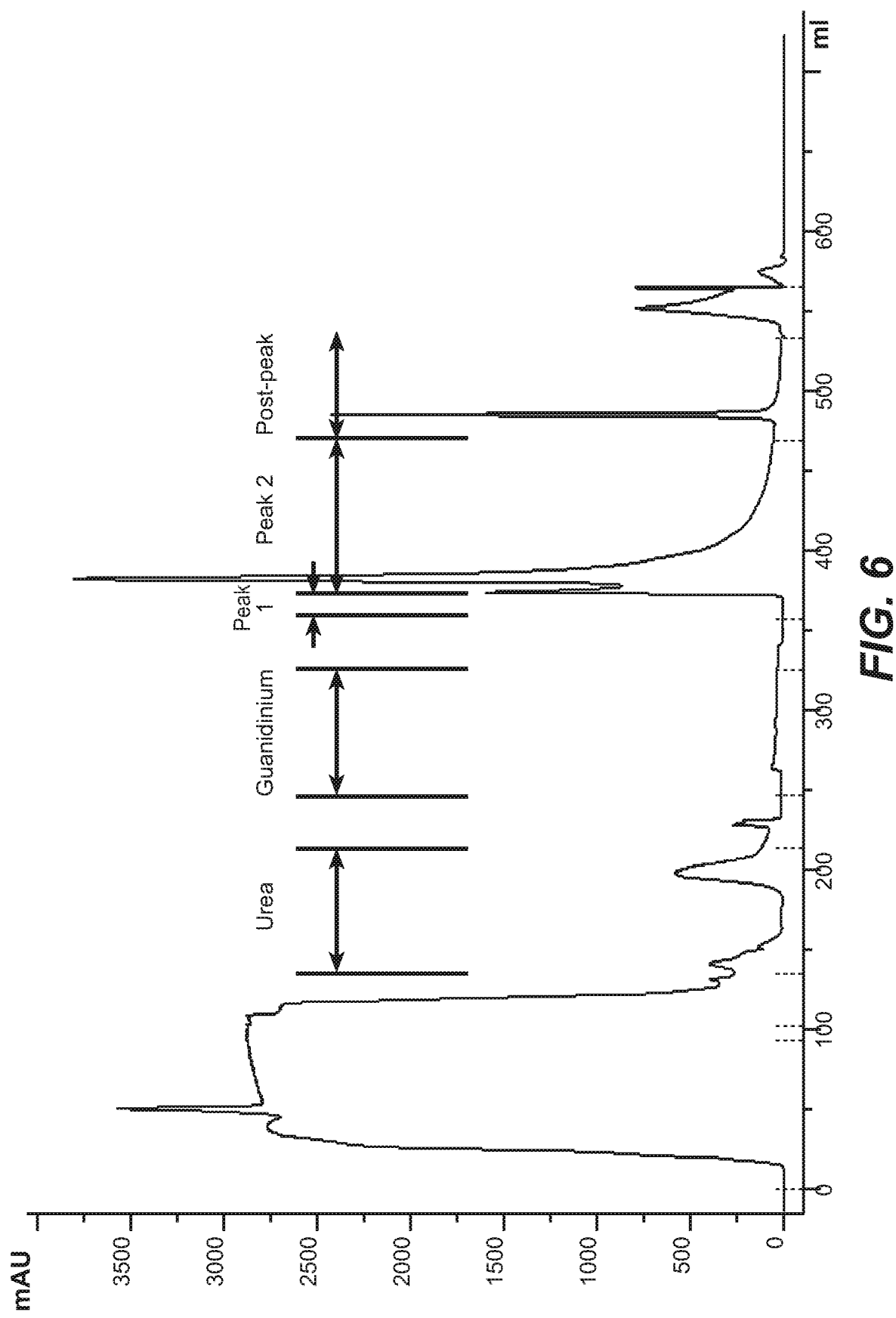
FIG. 6 Chromatogram of a purification of tetranectin-apolipoprotein A-I fusion protein of SEQ ID NO: 02 on an anion exchange chromatography column with urea wash, guanidinium hydrochloride wash and sodium chloride gradient elution.

Purification of Tetranectin-Apolipoprotein A-I Fusion Protein of SEQ ID NO: 02 on an Anion Exchange Chromatography Column with Urea Wash, Guanidinium Hydrochloride Wash and Sodium Chloride Gradient Elution resin: Q-Sepharose® FF (GE Healthcare)
load: 239 mg polypeptide column load: 15 mg/ml
equilibration: 30 mM potassium phosphate buffer pH 8.0; 5.9 mS/cm
urea wash: 6 M urea solution pH 8.0
guanidinium hydrochloride solution: 0.1 M guanidinium hydrochloride pH 8.0
elution solution: 0.35 M sodium chloride in 20 mM potassium phosphate buffer pH 8.0
wash steps:
  wash with 4 column volumes 6 M urea solution;
  wash with 4 column volumes 0.1 M guanidinium hydrochloride solution
elution method: step elution with 0.35 M sodium chloride for 7 column volumes
Result:
As can be seen from FIG. 6 in each of the wash steps only a minor fraction of the fusion protein can be obtained. The analytical results of three runs are shown in the following Table.

TABLE

| run | | DNA [pg/mg] | ECP [ng/ml] | LAL [EU/ml] | c (fusion protein) [mg/ml] | yield [%] |
|---|---|---|---|---|---|---|
| 1 | applied | 2280 | 477300 | 28115 | 2.6 | |
| 2 | solution | 2280 | 477300 | 28115 | 2.6 | |
| 3 | | 2833 | 108250 | 216531 | 1.2 | |
| 1 | peak 1 | n.d. | n.d. | n.d. | n.d. | 9.3 |
| 2 | | n.d. | n.d. | n.d. | n.d. | 16.1 |
| 3 | | n.d. | n.d. | n.d. | n.d. | 11.1 |
| 1 | peak 2 | 99 | 38550 | 263 | 0.8 | 31.7 |
| 2 | | 25 | 45200 | 670 | 1.0 | 35.1 |
| 3 | | 25 | 31920 | 38 | 0.9 | 37.1 |
| 1 | post peak | 66929 | 29520 | 22195 | 0.3 | 9.4 |
| 2 | | 23265 | 35900 | 928 | 0.3 | 12.7 |
| 3 | | 15619 | 11510 | 45 | 0.5 | 23.1 | n.d. = not determined

EXAMPLE 8A

Figure 7:
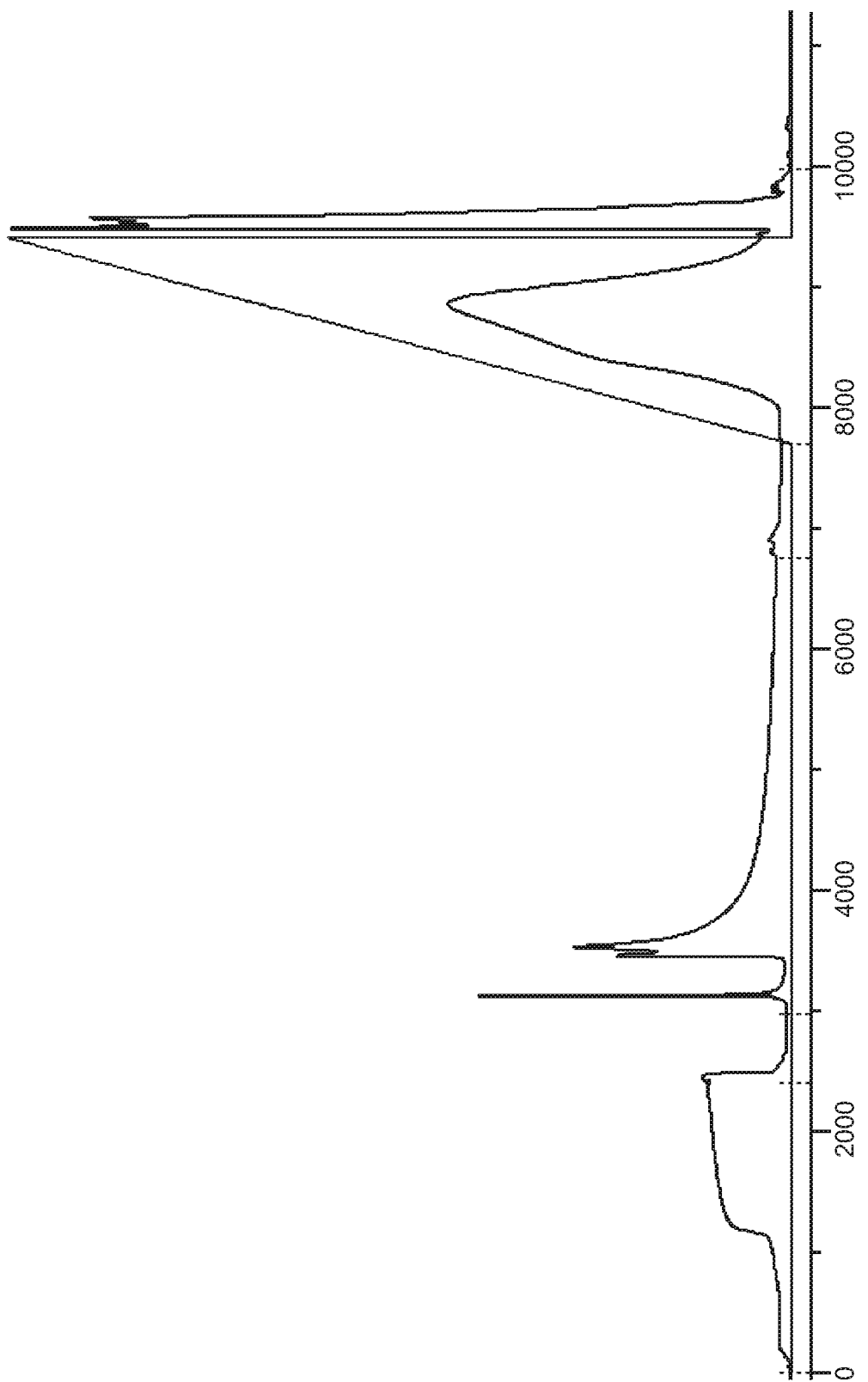
FIG. 7 Chromatogram of a purification of tetranectin-apolipoprotein A-I fusion protein of SEQ ID NO: 01 on a cation exchange chromatography column with urea gradient at constant conductivity and constant pH-value.

Purification of Tetranectin-Apolipoprotein A-I Fusion Protein of SEQ ID NO: 01 on a Cation Exchange Chromatography Column with Urea Gradient at Constant Conductivity and Constant pH-Value resin: POROS® HS
load: 5.58 g polypeptide
wash 1: 50 mM sodium formiate, adjusted to pH 3.0
wash 2: 1 M sodium chloride, 30 mM potassium phosphate buffer, adjusted to pH 8.0
wash 3: 30 mM potassium phosphate buffer, adjusted to pH 8.0
elution solution: 6 M urea in 10 mM potassium phosphate buffer pH 8.0
elution method:
  wash 1 for 3 column volumes,
  wash 2 for 20 column volumes,
  wash 3 for 5 column volumes,
  linear gradient 0 M to 6 M urea in 10 column volumes
Result:
As can be seen from FIG. 7 the fusion protein can be obtained in a defined peak. The analytical results are shown in the following Table.

TABLE

| | DNA [pg/mg] | ECP [ng/ml] | LAL [EU/ml] | c (fusion protein) [mg/ml] | yield [%] |
|---|---|---|---|---|---|
| applied solution | 1933426 | >99661 | 1712 | 3.3 | |
| recovered solution | 428784 | 145887 | 458 | 2.7 | 64.4 |

EXAMPLE 8B

Purification of Tetranectin-Apolipoprotein A-I Fusion Protein of SEQ ID NO: 01 on a Cation Exchange Chromatography Material Followed by an Anion Exchange Chromatography Column with Urea Gradient at Constant Conductivity and Constant pH-Value resin: POROS® HQ
load: 3.19 g polypeptide obtained in example 8a (see above)
Result:
The analytical results of the second chromatography step are shown in the following Table.

TABLE

| | DNA [pg/mg] | ECP [ng/ml] | LAL [EU/ml] | c (fusion protein) [mg/ml] | yield [%] |
|---|---|---|---|---|---|
| applied solution | 354545 | 81055 | 94 | 0.55 | |
| recovered solution | 6 | 203 | 6 | 4.3 | 82.8 |

EXAMPLE 9

Figure 8:
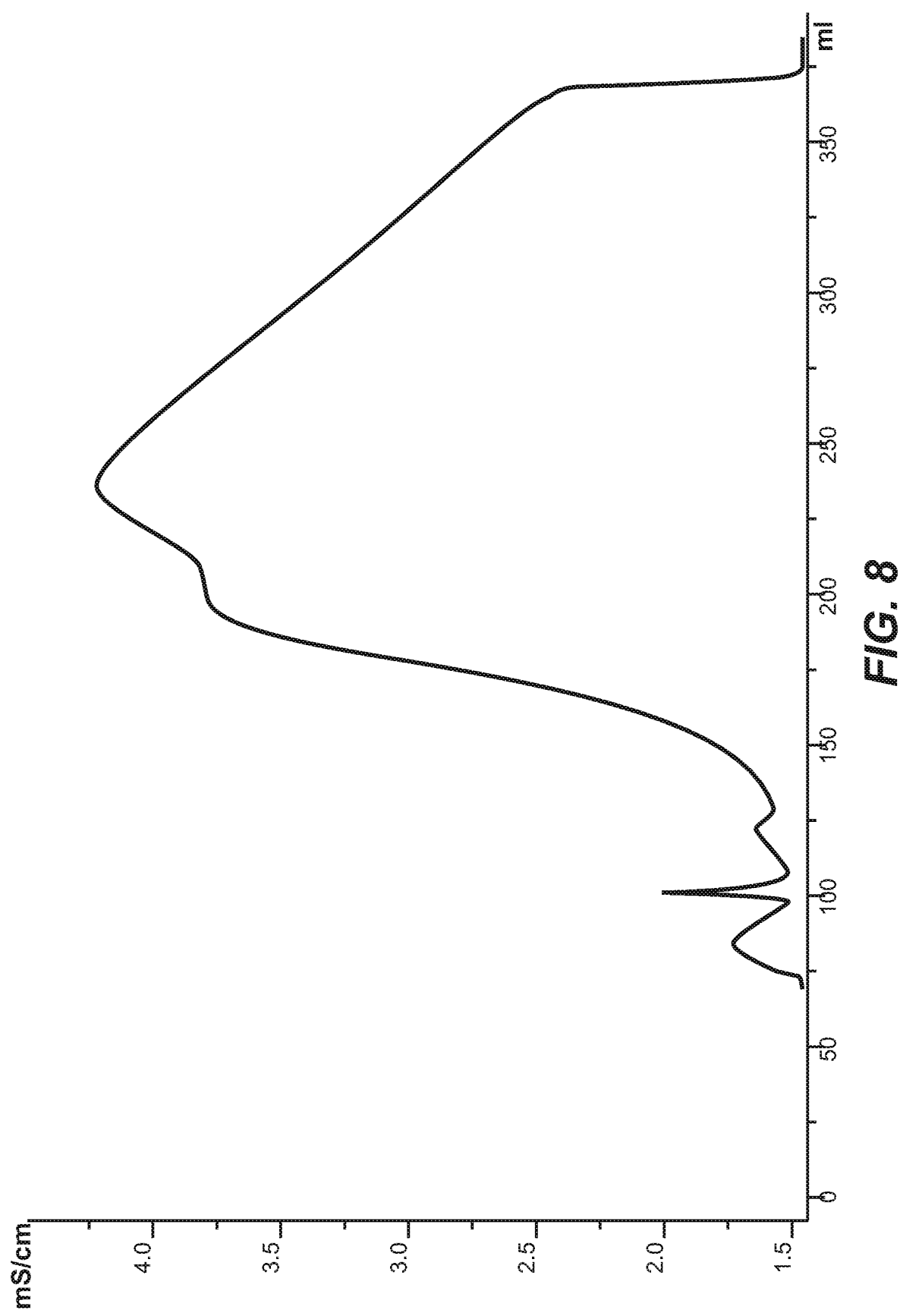
FIG. 8 Chromatogram of a purification of anti-TSLP receptor antibody on an anion exchange chromatography column with Tris buffer wash and urea gradient elution.

Purification of Anti-TSLP Receptor Antibody on an Anion Exchange Chromatography Column with Tris Buffer Wash and Urea Gradient Elution resin: POROSO HQ
load: 189 mg polypeptide
Tris wash: 5 mM Tris buffer with 10 mM sodium chloride pH 8.4; 4 mS/cm
elution solution: 5 mM Tris buffer with 10 mM sodium chloride and 6 M urea pH 8.4; 4 mS/cm
wash step: wash with 3 column volumes Tris buffer solution
elution method: linear gradient 0 M to 6 M urea in 30 column volumes
Result:
As can be seen from FIG. 8 the antibody can be obtained.

The invention claimed is:

1. A method for purifying a recombinantly produced polypeptide comprising the steps of:
    applying said polypeptide to a first ion exchange chromatography material in the absence of any denaturant and
    recovering said polypeptide with a solution comprising a gradient of a denaturant from said first ion exchange chromatography material at constant conductivity and constant pH and thereby purifying the polypeptide, wherein the denaturant is urea or an urea derivative, wherein the first ion exchange chromatography material comprises a matrix of cross-linked poly (styrene-divinylbenzene) to which ionic ligands have been attached.

2. The method of claim 1, characterized in that the ion exchange chromatography material is a cation exchange chromatography material.

3. The method of claim 2, characterized in that the ionic ligand is a sulfopropyl ligand or a carboxymethyl ligand.

4. The method of claim 1, characterized in that the ion exchange chromatography material is an anion exchange chromatography material.

5. The method of claim 4, characterized in that the ionic ligand is an ethyleneimine ligand or a quatemized ligand.

6. The method of claim 1, further comprising the steps of:
    following the recovering step, further applying the recovered polypeptide to a second ion exchange chromatography material, and
    recovering the polypeptide from the second ion exchange chromatography material by applying a second solution comprising the denaturant and thereby purifying the polypeptide.

7. The method according to claim 6, wherein
    the first ion exchange chromatography material is an anion exchange chromatography material and the second ion exchange chromatography material is a cation exchange chromatography material.

8. The method of claim 1, characterized in that the polypeptide has an amino acid sequence selected from the group of amino acid sequences of SEQ ID NO: 01, SEQ ID NO: 02, SEQ ID NO: 03, and SEQ ID NO: 04.

9. A method for producing a polypeptide comprising the following steps:
    cultivating a prokaryotic or eukaryotic cell comprising a nucleic acid encoding the polypeptide, recovering the polypeptide from the cells or/and the cultivation medium, purifying the polypeptide with an ion exchange chromatography method comprising the following steps applying the polypeptide to an ion exchange chromatography material in the absence of any denaturant, recovering the polypeptide with a solution comprising a gradient of denaturant from the ion exchange chromatography material at constant conductivity and constant pH and thereby producing a polypeptide, wherein the denaturant is urea or an urea derivative, whereby the ion exchange chromatography material comprises a matrix of cross-linked poly (styrene-divinylbenzene) to which ionic ligands have been attached.

10. The method of claim 9, characterized in that the denaturant is one denaturant and is selected from the group comprising urea, guanidine, urea-derivatives, and guanidine-derivatives.

11. The method of claim 9, characterized in that the ion exchange chromatography material is a cation exchange chromatography material.

12. The method of claim 11, characterized in that the ionic ligand is a sulfopropyl ligand or a carboxymethyl ligand.

13. The method of claim 9, characterized in that the ion exchange chromatography material is an anion exchange chromatography material.

14. The method of claim 13, characterized in that the ionic ligand is an ethyleneimine ligand or a quatemized ligand.

15. The method of claim 9, further characterized in comprising the following steps:

following the recovering step, further applying the recovered polypeptide to a second ion exchange chromatography material, and recovering the polypeptide from the second ion exchange chromatography material by applying a second solution comprising the denaturant and thereby obtaining or purifying the polypeptide.

16. The method according to claim 15, characterized in that the first ion exchange chromatography material is an anion exchange chromatography material and the second ion exchange chromatography material is a cation exchange chromatography material, or the first ion exchange chromatography material is a cation exchange chromatography material and the second ion exchange chromatography material is an anion exchange chromatography material.

17. The method of claim 15, characterized in that the recovered polypeptide is refolded prior to the applying to the second ion exchange chromatography material.

18. The method of claim 9, wherein the purifying further comprises the following step:

applying a first solution to the ion exchange chromatography material before applying the polypeptide to the ion exchange chromatography material, wherein the polypeptide is applied to the ion exchange chromatography material in a second solution and the polypeptide is recovered with a fourth solution comprising a denaturant, whereby the first solution comprises a first buffer substance, the second solution comprises a second buffer substance, and the fourth solution comprises a fourth buffer substance and the denaturant.

19. The method of claim 9, characterized in that the polypeptide has an amino acid sequence selected from the group of amino acid sequences of SEQ ID NO: 01, SEQ ID NO: 02, SEQ ID NO: 03, and SEQ ID NO: 04.

20. The method of claim 9, wherein the denaturant is a urea or a urea-derivate.

21. A method for purifying a recombinantly produced polypeptide comprising the steps of:

applying a first solution to a first ion exchange chromatography material, applying a second solution comprising the polypeptide to the first ion exchange chromatography material in the absence of any denaturant, and recovering and thereby purifying the polypeptide, at constant conductivity and constant pH, with a fourth solution, wherein the first ion exchange chromatography material comprises a matrix of cross-linked poly (styrene-divinylbenzene) to which ionic ligands have been attached, and wherein the first solution comprises a first buffer substance substantially free of denaturant, the second solution comprises a second buffer substance substantially free of denaturant, and the fourth solution comprises a fourth buffer substance, wherein the fourth buffer substance comprises a gradient of a denaturant selected from the group consisting of urea or a urea derivative.

22. The method according to claim 21, characterized in that after applying the second solution and prior to applying the fourth solution the following step is added:

applying a third solution to the ion exchange chromatography material, whereby the third solution comprises a third buffer substance.

* * * * *